United States Patent [19]

Horodysky

[11] 4,207,195

[45] Jun. 10, 1980

[54] SULFURIZED OLEFIN ADDUCTS OF DIHYDROCARBYL PHOSPHITES AND LUBRICANT COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 905,269

[22] Filed: May 12, 1978

[51] Int. Cl.$^2$ ........................ C10M 1/48; C07G 17/00
[52] U.S. Cl. .................................. 252/46.6; 260/139; 260/970; 252/400 A
[58] Field of Search ......................... 252/46.6, 400 A; 260/970, 139

[56] References Cited

U.S. PATENT DOCUMENTS

| | | | |
|---|---|---|---|
| 2,110,281 | 3/1938 | Adams et al. ........................... | 252/45 |
| 3,017,346 | 1/1962 | Watson ............................. | 260/970 X |
| 3,029,272 | 4/1962 | Runge ................................. | 260/970 |
| 3,115,465 | 12/1963 | Orloff et al. ......................... | 252/49.9 |
| 3,329,742 | 7/1967 | Myers ............................. | 252/49.8 X |
| 3,446,739 | 5/1969 | Papay ................................ | 252/49.8 |
| 3,510,426 | 5/1970 | Papay ................................ | 252/46.6 |
| 3,583,915 | 6/1971 | Myers ................................ | 252/46.6 |
| 3,812,222 | 5/1974 | Kleiner et al. ....................... | 260/970 |
| 3,899,475 | 8/1975 | Hotten .............................. | 252/46.6 X |
| 3,909,429 | 9/1975 | McClaflin ......................... | 252/46.6 X |
| 3,914,345 | 10/1975 | Kleiner et al. ....................... | 260/970 |
| 3,933,658 | 1/1976 | Beiswanger et al. ........... | 252/46.6 X |
| 4,152,275 | 5/1979 | Horodysky et al. ................ | 252/46.6 |

Primary Examiner—Thomas A. Waltz
Attorney, Agent, or Firm—Charles A. Huggett; Raymond W. Barclay; Claude E. Setliff

[57] ABSTRACT

Dihydrocarbyl phosphites are reacted with sulfurized olefins to give products useful as antiwear and antioxidant additives for lubricants. Organic compositions containing a minor amount thereof also possess good lubricating characteristics.

20 Claims, No Drawings

SULFURIZED OLEFIN ADDUCTS OF DIHYDROCARBYL PHOSPHITES AND LUBRICANT COMPOSITIONS CONTAINING SAME

BACKGROUND OF THE INVENTION

1. Field of the Invention

The invention relates to novel compounds, particularly to those comprising reaction products of dihydrocarbyl phosphites and a sulfurized olefin, and to lubricant compositions containing same.

2. Discussion of the Prior Art

It is well-known that lubricants tend to oxidize when exposed to adverse storage conditions or in actual use. It is also known that lubricated parts themselves are subject to wearing and to corrosion. Deterioration of lubricant in service and excessive wear and corrosion of the lubricated surfaces results in the formation of gums, sludges and other deposits which clog the feed lines and form varnish-like deposits on operating surfaces. At the very least these will decrease the efficiency of, for example, an engine, and in extreme cases may lead to a totally inoperative machine.

Organic sulfur compounds have been known as additives for lubricating oils. They are generally used to provide extreme pressure properties to lubricants, especially under high-speed shock conditions. For example, sulfurized olefins are a known class of such organic sulfur compounds. Their utility and methods of preparation are disclosed in U.S. Pat. Nos. 3,471,404, 3,697,499 and 3,703,504.

Certain phosphorus compounds are also known lubricant additives. Furthermore, the art is replete with examples of addition of olefins to hydrogen phosphites under the influence of a catalyst. However, no art is known which teaches or suggests the adducts of this invention.

SUMMARY OF THE INVENTION

The invention provides a product of reaction between a dihydrocarbyl phosphite of the general formula

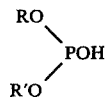

wherein R and R' are hydrocarbyl groups and are the same or different with each having 1 to 30 carbon atoms. Thus, R and R' may each be alkyl of 1 to about 30 carbon atoms, or aryl, alkaryl or aralkyl of 6 to about 30 carbon atoms. Thus, phosphites wherein R and R' include methyl, ethyl, n-propyl, isopropyl, n-butyl, isobutyl, pentyl, amyl, hexyl, ethylhexyl, oleyl, phenyl, naphthyl and the like, and mixtures thereof may be reacted with a sulfurized olefin containing reactive olefinic sites. The sulfurized olefin may be derived from a process comprising sulfohalogenating a hydrocarbon olefin having a single double bond and having from 2 to about 8 carbon atoms per molecule with a sulfur halide selected from the group consisting of sulfur chlorides and sulfur bromides to form a sulfohalogenated intermediate and thereafter sulfurizing and dehalogenating the intermediate by treatment with an aqueous metal monosulfide solution such as described in U.S. Pat. No. 3,703,504. Or it may be derived by any other generally known process such as the reaction of an olefinic halide like methallyl chloride with a metal monosulfide, metal disulfide or a metal polysulfide. The reaction products of dihydrocarbyl phosphites and sulfurized olefins contain 0.01 to 10% sulfur depending upon the specific reactants chosen and their reaction ratios.

The invention also provides a lubricant composition containing such products.

DESCRIPTION OF SPECIFIC EMBODIMENTS

As stated hereinabove, the dihydrocarbyl phosphite useful in the practice of this invention has the formula

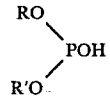

wherein R and R' are hydrocarbyl groups and are the same or different, with each having from 1 to 30 carbon atoms. The R and R' may each be alkyl of 1 to about 30 carbon atoms, aryl, alkaryl or aralkyl of 1 to about 30 carbon atoms. Preferably, the hydrocarbyl groups are alkyl groups.

Sulfurized olefins useful herein are generally described in U.S. Pat. No. 3,703,504, the entirety of which is incorporated herein by reference. This class of reactant, however, is not limited to such patent. Other sulfurized olefins made by variations of this process or by other processes known to the art which contain reactive olefinic sites may also be employed in this invention.

The sulfurized olefins may be obtained via a process which comprises sulfohalogenating an olefin with a sulfur halide in the presence of a catalytic quantity of a lower aliphatic alcohol, or other appropriate catalyst to form a sulfohalogenated organic intermediate, and thereafter sulfurizing and dehalogenating said intermediate in the presence of a substantial quantity of lower aliphatic alcohol by treatment with an aqueous alkali metal sulfide solution, or an aqueous alkali metal monosulfide solution (which can be derived, for example, from a spent aqueous alkali metal hydroxide effluent from hydrocarbon purification) having a substantial combined sulfur content thus producing an organic sulfide of high sulfur content.

A wide variety of olefinic substances may be charged to the initial or sulfochlorination reaction including olefins having a single double bond with terminal or internal double bonds and containing from about 2 to 8 or more carbon atoms per molecule in either straight, branched chain or cyclic compounds, and these may be exemplified by ethylene, propylene, butene-1, cis and trans butene-2, isobutylene, diisobutylene, triisobutylene, the pentenes, cyclopentene, the hexenes, cyclohexene, the octenes, decene-1, etc. In general, $C_3$-$C_6$ olefins or mixtures thereof are desirable for preparing sulfurized products for use in preparing the inventive additives. We prefer these since the combined sulfur content of the product decreases with increasing carbon content yet its miscibility with oil is lower for propylene and ethylene derivatives.

In some embodiments of the invention, isobutylene is particularly preferred as the sole olefinic reactant, but it may be employed, desirably in major proportion, in mixtures containing one or more other olefins; moreover, the charge may contain substantial proportions of saturated aliphatic hydrocarbons as exemplified by methane, ethane, propane, butanes, pentanes, etc. Such alkanes are preferably present in minor proportion in most instances to avoid unnecessary dilution of the reaction, since they neither react nor remain in the products but are expelled in the off-gases or by subsequent distillation. However, mixed charges can substantially improve the economics of the present process since such streams are of lower value than a stream of relatively pure isobutylene.

Volatile olefins are often readily available in liquid form, and it is usually desirable to charge olefinic liquids which are vaporized by the heat of reaction, as such evaporation provides a substantial cooling effect that permits the flow of water for cooling the reactor to be reduced considerably for greater economy. Also there are indications that the use of a volatile liquid olefin reactant has the unexpected effect of lowering the viscosity of the final product.

The other reactant in the first stage is preferably sulfur monochloride ($S_2Cl_2$), but other similar compounds, such as sulfur dichloride and $S_3Cl_2$, as well as the corresponding but more expensive sulfur bromides, may be employed in an amount which will provide a quantity of sulfur corresponding to desirable reactant ratios for sulfur monochloride. The reaction is carried out by reacting one mole of the chloride with from about 1 to about 2, preferably from about 1.25 to about 1.8, moles of olefin.

Although anhydrous reaction conditions are generally regarded as providing better results, a small amount of water ranging up to about 10% of the weight of the sulfur halide may be present in the initial reaction; however, it is usually preferred to keep the water content below about 4% on that basis.

The sulfohalogenation reaction is exothermic, evolving 500–650 b.t.u./lb. in the case of isobutylene, and cooling is necessary to prevent the temperature from exceeding about 160° F. with resultant darkening of the product and some decrease in the yield. The preferred range of reaction temperatures is from about 120° to 135° F. and a temperature of about 125° F. appears to be the optimum. Typical reaction times for the initial stage of the process range from about 1 to 15 hours.

The reaction pressure is not critical here and may be illustrated by pressures ranging from about 0 to 100 pounds per square inch gage pressure (p.s.i.g.) depending upon the reaction temperature and the volatility of the olefinic material.

The initial reaction may be catalyzed to improve product yield with a lower aliphatic alcohol containing from 1 to 4 carbon atoms, as exemplified by methanol, ethanol, propanol and isopropanol. Of these, methanol and ethanol are usually preferred, especially the former. The amounts of the alcohol ranging from about 0.2 to 10% of the weight of the sulfur chloride may be utilized, but quantities of the order of 0.5 to 3% are usually preferred. While the catalytic alcohol may be introduced into the reactor in the liquid state, it is often more desirable to introduce it as a vapor.

Following completion of the reaction between olefin and sulfur chloride, such product is then reacted with an alkali metal sulfide.

In this reaction, the adduct is combined with a mixture of the alkali metal sulfide, preferably sodium sulfide. The mole ratio of alkali metal sulfide to adduct is about 0.8 to about 1.2 moles of metal sulfide per mole of adduct. This ratio is considered significant in the practice of this invention. It has been found to contribute to the oil solubility and thermal stability of the final product. This reaction, furthermore, may be carried out in the presence of an alcohol or an alcohol-water solvent under reflux conditions. The alcohol may be present in a concentration in the water of from 5 percent to 50 percent by weight. Water-soluble alcohols, such as methanol, ethanol, propanol, isopropanol, butanol, and the like, may be used. The reflux time ranges from 3 to 6 hours.

The exact structure of the product is not known. It may consist of monomers containing sulfur or monomers bridged in a cyclic structure by the sulfur. It is believed that about 75% or more of the product is made up of monomeric sulfides and the cyclic derivatives thereof. An important feature of these oil-soluble polysulfurized olefins is that the products contain from about 30 to about 60%, preferably 46 to 48%, sulfur in stabilized form, and less than 0.5% chlorine.

Dihydrocarbyl phosphites can be added in low concentrations to the unsaturated components of certain sulfurized olefins to form low phosphorus (0.1–10%) high sulfur (about 20% or more) content products. The products thus formed impart good antiwear and antioxidant activity to organic substrates, e.g., lubricating oils, when incorporated therein. The dihydrocarbyl phosphate moiety incorporated with the sulfurized olefin may account for a significant portion of the antiwear and antioxidant activity.

Dihydrocarbyl phosphites are reacted with sulfurized olefins in the presence of an appropriate free radical or peroxide-type catalyst or azo-type initiator. Preferred catalysts include 2,2'-azobisisobutyronitrile and t-butylperoxybenzoate. Other less active catalysts include benzoyl peroxide, t-butyl peroxide and 2,2'-azobis(2-amidinopropane) HCl. As little as 0.01% mole or up to 100% mole and more of dihydrocarbyl phosphite per mole of reactive olefin contained in the sulfurized olefin can be used in this reaction. It is preferred, however, to use 10–50% mole of dihydrocarbyl phosphite based upon reactive olefin. The reactants can be added in any order but the sequential addition of sulfurized olefin and catalyst to dihydrocarbyl phosphite at reaction temperature is preferred. The reaction mixture is then stirred until all of the catalyst is decomposed and the reaction is completed. The reaction temperature used can be from 0°–150° C. and is chosen primarily based upon the predicted reactivity and half-life of the catalyst. For most of the reactive catalysts, temperatures of 50°–120° C. are preferred. Solvents can be used to accelerate the reaction. The lower molecular weight alcohols such as isopropanol can be used as reaction solvents. It is generally helpful to exclude air from the reaction system. This can be done with the use of an inert gas purge such as nitrogen. Reaction times can be short or as long as 20 hours depending especially on the choice of catalyst and the reaction temperature. After the reaction is essentially complete, as evidenced by the consumption of the catalyst and decreases in the concentration of the dihydrocarbyl phosphite and the reaction olefin group in the sulfurized olefins, the product can be worked up by removal of the solvent and unreacted dihydrocarbyl phosphite. The solvent and dihydrocarbyl phosphite can be removed by distillation if volatile or by water extraction if water soluble. Residual higher molecular weight dihydrocarbyl phosphite can be left in the product mixture. Water washing, however, is generally performed to remove aqueous soluble by-product. The washed product can then be dried by heating in vacuo and filtered to give a clear, viscous liquid.

The lubricants which may be improved by the adducts are mineral and synthetic lubricating oils and greases made therefrom. The mineral oils embrace not only the paraffinic members, but also the naphthenic members. By synthetic oils are meant those including synthetic hydrocarbon fluids, polyalkylene oxide oils, polyacetals, polysilicones and the like, as well as the synthetic ester oils. With reference to the latter type there may be mentioned those esters made from monohydric alcohols and polycarboxylic acids, such as 2-ethylazelate and the like, and those made from polyhydric alcohols and aliphatic monocarboxylic acids. Those of this group are very important, and they include esters prepared from (1) the trimethylols, such as the ethane, propane and butane derivatives, 2,2-disubstituted propane diols and the pentaerythritols and (2) aliphatic monocarboxylic acids containing from 4 to 9 carbon atoms. Mixtures of these acids may be used to prepare the esters. An example of such esters is one prepared from pentaerythritol and a mixture of $C_5$-$C_9$ acids.

Having described the invention in general terms, the following are offered as illustrations.

EXAMPLE 1

Preparation of Sulfurized Olefin

Sulfurized olefin was prepared in accordance with Example 1 of U.S. Pat. No. 3,703,504 using isobutylene. The yield of sulfurized organic product amounted to 98% of theory, had a sulfur content of 47% by weight and a chlorine content of only 0.1% as well as a clear, light orange brown color, and a high flash point of 250° F.

EXAMPLE 2

Preparation of Sulfurized Olefin

Sulfurized olefin was prepared in general accordance with Example 6 of U.S. Pat. No. 3,703,504. A mixture of sulfurized organic compounds using mixed butylene reactants obtained from a petroleum refinery stream instead of isobutylene was obtained using the same reaction conditions and molar ratios of reactants. Ignoring the small water content, the predominantly olefinic mixture employed in this instance had the following composition by volume:

| Component | Volume Percent |
| --- | --- |
| Propylene | 0.2 |
| Propane | 1.0 |
| Isobutane | 3.4 |
| Butane | 10.5 |
| Isobutylene | 48.2 |
| Butene-1 | 31.5 |
| Trans-2-butene | 4.1 |
| Cis-2-butene | 0.2 |
| Butadiene | 0.4 |
| Methylacetylene | 0.1 |
| Other hydrocarbons | 0.4 |
| | 100.0 |

The product obtained by reacting the tabulated hydrocarbon mixture was more complex than that obtained with the isobutylene reactant; however, its properties resemble those of the product of Example 1 as evidenced by the following characteristics.

Sulfur content—47%
Chlorine content—0.1%
Viscosity—12.3 cs/210° F.

EXAMPLE 3

Preparation of Adduct

Sulfurized olefin (400 g.) containing reactive olefin groups prepared in accordance with Example 1 was reacted with 120 g. of dimethyl hydrogen phosphite at 90° to 100° C. using 10 g. of 2,2'-azobisisobutyronitrile as catalyst for a total of 10 hours with agitation. A slow nitrogen purge was used during the reaction period. The crude product was washed 4 times with a total of 1200 ml. of water and was vacuum dried at 100° C. and filtered. A pale yellow liquid having a very low odor was isolated. The product contained 36.4% by weight of sulfur and 0.70% by weight of phosphorus.

EXAMPLE 4

Sulfurized olefin (250 g.) containing reactive olefin groups prepared in accordance with Example 2 was reacted with 60 g. of dimethyl hydrogen phosphite using 20 g. of 2,2'-azobisisobutyronitrile at 90° to 100° C. for about 4 hours. Approximately 50 ml. isopropanol was added as a reaction solvent. Premixed sulfurized olefin and catalyst were added to the heated dimethyl hydrogen phosphite to initiate the reaction. The reaction mixture was heated to 100° C. in vacuum to remove isopropanol solvent and volatile by-products. An equal amount of pentane was added and the product was water washed 4 times. The product was then dried by heating to 100° C. in vacuum to remove pentane and water and was filtered. A pale yellow liquid containing 40.8% by weight of sulfur, 0.60% by weight of phosphorus, 47.47% by weight of carbon and 7.17% by weight of hydrogen was recovered.

EXAMPLE 5

Sulfurized olefin (200 g.) prepared as described in Example 1 was reacted with 60 g. of dimethyl hydrogen phosphite using 15 g. of 2,2'-azobisisobutyronitrile and 25 ml. of isopropanol. After a 4-hour reaction period at 65° C. with agitation and a nitrogen sparge, the reaction mixture was heated to 115° C. At this point, a second catalyst, benzoyl peroxide was added and the reaction mixture was held at 130° C. for 4 hours. The volatile solvent and by-products were removed by distillation and the crude product was water washed 4 times, dried by heating to 100° C. in vacuum and filtered. The pale yellow liquid contained 39.9% by weight of sulfur, 1.84% by weight of phosphorus, 45.19% by weight of carbon and 7.35% by weight of hydrogen.

EXAMPLE 6

Sulfurized olefin (225 g.) prepared as described in Example 1 was reacted with 50 g. of dimethyl hydrogen phosphite using 15 g. of t-butylperoxybenzoate as catalyst. After an 8-hour reaction period at 90° to 110° C. with agitation and a nitrogen sparge, the volatile by-products and unused reactants were removed by distillation in vacuum. The crude product was water washed 4 times, dried by heating to 100° C. in vacuum and filtered. The pale yellow liquid contained 40.4% by weight of sulfur, 1.71% by weight of phosphorus, 47.03% by weight of carbon and 7.42% by weight of hydrogen.

EXAMPLE 7

Sulfurized olefin (190 g.) prepared as described in Example 1 was reacted with 90 g. of dibutyl hydrogen phosphite and 16 g. of t-butylperoxybenzoate. The reaction mixture was agitated at 100° to 110° C. for 4 hours and 2 hours at 120° to 125° C. using a nitrogen sparge. The volatile by-products were removed by distillation at 120° to 125° C. in vacuum. The crude product was water washed 4 times, dried by heating in vacuum and filtered. The pale yellow liquid contained 37.4% by weight of sulfur, 1.91% by weight of phosphorus, 46.94% by weight of carbon and 7.19% by weight of hydrogen.

EVALUATION OF PRODUCTS

Antioxidant Test

In this test, samples of 200 second solvent paraffinic neutral oil containing the additive and samples of sand-biased iron wire, polished copper wire, polished aluminum wire, polished lead surfaces are heated to 325° F. and dry air at the rate of about 5 liters per hour is passed through the lubricant for 40 hours. The samples are observed for increase in acidity ($\Delta$NN) and kinematic viscosity ($\Delta$KV) before and after treatment. Other things, such as loss in weight of metal specimen or sludge content, may also be observed.

TABLE 1

Catalytic Oxidation Test (325° F., 40 Hours)

| Example No. | Concentration of Additive | Pb Loss, mg. | Percent Increase in Viscosity of oxidized oil, KV at 210° F. | Neutralization Number (NN) of Oxidized Oil |
|---|---|---|---|---|
| Base Stock, (200" solvent paraffinic neutral) | 0% | 0.4 | 27 | 2.21 |
| Example 3 | 1% | 0.0 | 12 | 1.68 |
| Example 3 | 3% | 0.3 | 7 | 1.14 |
| Example 4 | 1% | 0.1 | 13 | 1.83 |
| Example 4 | 3% | 0.0 | 7 | 1.42 |
| Example 5 | 1% | 0.1 | 6 | 2.10 |
| Example 5 | 3% | 0.0 | 4 | 1.65 |
| Example 6 | 1% | 0.0 | 11 | 1.24 |
| Example 6 | 3% | 0.0 | 14 | 1.48 |
| Example 7 | 1% | 0.0 | 15 | 1.71 |
| Example 7 | 3% | 0.0 | 21 | 0.49 |

Shell Four-Ball Test

The product was added to a mineral oil and was tested in this well-known test. The balls were ½" 52100 steel and were tested for 30 minutes at a load of 60 kg. The following table summarizes the data obtained:

TABLE 2

| Additive | Conc., Wt. % | Temp., °C. | RPM | | | |
|---|---|---|---|---|---|---|
| | | | 500 | 1000 | 1500 | 2000 |
| None* | 100 | Room | 0.50 | 0.60 | 0.88 | 2.34 |
| | 100 | 200 | 0.60 | 1.06 | 1.86 | 2.23 |
| | 100 | 390 | 1.00 | 1.31 | 2.06 | 0.90 |
| Example 4 | 1.0 | Room | 0.50 | 0.80 | 0.90 | 1.10 |
| | 1.0 | 200 | 0.85 | 0.70 | 0.82 | |
| Example 5 | 1.0 | Room | 0.45 | 0.60 | — | 1.05 |
| | 1.0 | 200 | — | 0.70 | — | 1.00 |
| | 1.0 | 390 | — | 1.25 | — | 1.75 |

*The base oil containing no adduct was a mixture of 80% of a 150 second solvent paraffinic bright and of 20% of a 200 second solvent paraffinic neutral oils. The adduct was used in this same oil.

I claim:

1. A product obtained by the reaction of a dihydrocarbyl phosphite of the formula

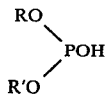

wherein R and R' are the same or different $C_1$-$C_{30}$ hydrocarbyl groups with a sulfurized olefin in the presence of a free-radical or peroxide type catalyst for the said reaction.

2. The product of claim 1 wherein R and R' are selected from a $C_1$-$C_{30}$ alkyl or a $C_6$-$C_{30}$ aryl, alkaryl or aralkyl.

3. The product of claim 1 wherein R and R' are selected from methyl, ethyl, propyl, butyl, pentyl, amyl, hexyl, ethylhexyl, oleyl, phenyl and naphthyl.

4. The product of claim 1 wherein the sulfurized olefin is derived from the sulfohalogenation of a $C_2$-$C_8$ olefin.

5. The product of claim 1 containing from about 0.01 to about 10% by weight of phosphorus and from about 10 to about 50% by weight of sulfur.

6. The product of claim 1 wherein R and R' are methyl.

7. The product of claim 1 wherein R and R' are butyl.

8. The product of claim 1 wherein the catalyst is 2,2'-azobisisobutyronitrile.

9. The product of claim 1 wherein the catalyst is t-butylperoxybenzoate.

10. The product of claim 1 wherein the catalyst is a mixture of 2,2'-azobisisobutyronitrile and benzoyl peroxide.

11. A lubricant composition comprising a major proportion of a lubricant and an antiwear or antioxidant amount of a product obtained by the reaction of a dihydrocarbyl phosphite of the formula

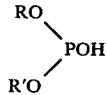

wherein R and R' are the same or different $C_1$-$C_{30}$ hydrocarbyl groups with a sulfurized olefin in the presence of a free-radical or peroxide type catalyst for the said reaction.

12. The composition of claim 11 wherein R and R' are selected from a $C_1$-$C_{30}$ alkyl or a $C_6$-$C_{30}$ aryl, alkaryl or aralkyl.

13. The composition of claim 11 wherein R and R' are selected from methyl, ethyl, propyl, butyl, pentyl, amyl, hexyl, ethylhexyl, oleyl, phenyl and naphthyl.

14. The composition of claim 11 wherein the sulfurized olefin is derived from the sulfohalogenation of a $C_2$-$C_8$ olefin.

15. The composition of claim 11 wherein the product contains from about 0.01 to about 10% by weight of phosphorus and from about 10 to about 50% by weight of sulfur.

16. The composition of claim 11 wherein R and R' are methyl.

17. The composition of claim 11 wherein R and R' are butyl.

18. The composition of claim 11 wherein the lubricant is a lubricating oil or a grease therefrom.

19. The composition of claim 18 wherein the lubricating oil is a mineral oil.

20. The composition of claim 18 wherein the lubricating oil is a synthetic hydrocarbon fluid.

UNITED STATES PATENT AND TRADEMARK OFFICE
CERTIFICATE OF CORRECTION

PATENT NO. : 4,207,195
DATED : June 10, 1980
INVENTOR(S) : ANDREW G. HORODYSKY

It is certified that error appears in the above—identified patent and that said Letters Patent are hereby corrected as shown below:

Col. 2, line 5, after "10%" insert --phosphorus and 10 to 50%--.

Col. 7, line 20, change "biased" to --blasted--.

Signed and Sealed this

Twenty-eighth Day of October 1980

[SEAL]

Attest:

SIDNEY A. DIAMOND

Attesting Officer

Commissioner of Patents and Trademarks